US006111158A

United States Patent [19]
Marinangeli et al.

[11] Patent Number: 6,111,158
[45] Date of Patent: Aug. 29, 2000

[54] PROCESS FOR PRODUCING ARYLALKANES AT ALKYLATION CONDITIONS USING A ZEOLITE HAVING A NES ZEOLITE STRUCTURE TYPE

[75] Inventors: Richard E. Marinangeli, Arlington Heights; Michael G. Gatter, Elk Grove Villate; R. Joe Lawson, Arlington Heights; Thomas R. Fritsch, Villa Park, all of Ill.

[73] Assignee: UOP LLC, Des Plaines, Ill.

[21] Appl. No.: 09/262,249

[22] Filed: Mar. 4, 1999

[51] Int. Cl.$^7$ .............................. C07C 2/68; C07C 2/64; C07C 25/107
[52] U.S. Cl. ........................................... 585/467; 585/455
[58] Field of Search ...................... 585/467, 455

[56] References Cited

U.S. PATENT DOCUMENTS

| | | | |
|---|---|---|---|
| 5,041,402 | 8/1991 | Casci et al. | 502/67 |
| 5,102,641 | 4/1992 | Casci et al. | 423/328 |
| 5,178,748 | 1/1993 | Casci et al. | 208/46 |
| 5,446,234 | 8/1995 | Casci et al. | 585/467 |
| 5,641,393 | 6/1997 | Nakagawa | 208/46 |

FOREIGN PATENT DOCUMENTS

| | | | |
|---|---|---|---|
| WO 99/05082 | 2/1999 | WIPO | C07C 5/27 |
| WO 99/05084 | 2/1999 | WIPO | C07C 29/16 |
| WO 99/05241 | 2/1999 | WIPO | C11D 1/22 |
| WO 99/05243 | 2/1999 | WIPO | C11D 1/22 |

OTHER PUBLICATIONS

*Handbook of Petroleum Refining Processes* edited by Robert A. Meyers, (McGraw–Hill, New York, 2$^{nd}$ Ed., 1997) pp. 1.53–1.66 and pp. 5.11–5.19.

Temperature programmed Capillary Gas Chromatography of Complex Hydrocarbon Mixtures $C_3$ to $C_{16}$ Dependence of Col. Efficiency (Separation Number) on C–Number, Temperature and Heating Rate H. Schulz/H.O. Reitemeyer, Institut fur Gastechnik, Feuerunjgstechnik und Wasserchemie, Universitat Karlsruhe, D–75 Karlsruhe (Chromatographia 1, 1968) pp. 315–3326.

*Atlas of Zeolite Structure Types* W.M. Meier et al., (Elsevier 4$^{th}$ Rev. Ed.) pp. 162–163 ISBN 0–444–10015–6.

High Resolution Mulipulse NMR Spectrum Editing and DEPT W.–Germany Bruker Analytische Messtechnik GMBH.

Gottardiite, a new high–silica zeolite from Antartica: the natural counterpart of synthetic NU–87 E. Galli et al. (Eur.J. Mineral. 1996, 8. pp. 687–693).

Structure of the two–dimensional medium–pore high–silica zeolite NU–87 M.D. Shannon, et al. Nature vol. 353 Oct. 3, 1991 pp.417–420.

The crystal structure of gottardiite, a new natural zeolite Alberto Alberti et al. (Eur.J. Mineral. 1996, 8, pp. 69–75).

*Primary Examiner*—Jacqueline V. Howard
*Assistant Examiner*—Thuan D. Dang
*Attorney, Agent, or Firm*—John G. Tolomei; Michael A. Moore

[57] ABSTRACT

The present invention is a process for producing phenyl-alkanes at alkylation conditions in the presence of a zeolite having an NES zeolite structure type, such as NU-87. This invention produces phenyl-alkanes having lightly branched aliphatic alkyl groups which are used to produce modified alkylbenzene sulfonates that have improved cleaning effectiveness in hard and/or cold water while also having biodegradability comparable to that of linear alkylbenzene sulfonates.

18 Claims, No Drawings

PROCESS FOR PRODUCING ARYLALKANES AT ALKYLATION CONDITIONS USING A ZEOLITE HAVING A NES ZEOLITE STRUCTURE TYPE

FIELD OF THE INVENTION

The invention relates generally to the alkylation of aryl compounds with olefins using solid catalyst, and more specifically to a process for selectively producing particular arylalkanes using a zeolitic catalyst.

BACKGROUND OF THE INVENTION

More than about thirty years ago, many household laundry detergents were made of branched alkylbenzene sulfonates (BABS). BABS are manufactured from a type of alkylbenzenes called branched alkylbenzenes (BAB). Alkylbenzenes (phenyl-alkanes) refers to a general category of compounds having an aliphatic alkyl group bound to a phenyl group and having the general formula of $(m_i\text{-alkyl}_i)_i$-n-phenyl-alkane. The aliphatic alkyl group consists of an aliphatic alkyl chain, which is referred to by "alkane" in the $(m_i\text{-alkyl}_i)_i$-n-phenyl-alkane formula. Of the chains of the aliphatic alkyl group, the aliphatic alkyl chain is the longest straight chain that has a carbon bound to the phenyl group. The aliphatic alkyl group may also consist of one or more alkyl group branches, each of which is attached to the aliphatic alkyl chain and is designated by a corresponding "$(m_i\text{-alkyl}_i)_i$" in the $(m_i\text{-alkyl}_i)_i$-n-phenyl-alkane formula. If it is possible to select two or more chains of equal lengths as the aliphatic alkyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $m_i$ of the aliphatic alkyl chain. The phenyl group is attached to the aliphatic alkyl group, specifically to carbon number n of the aliphatic alkyl chain. The aliphatic alkylation chain is numbered from one end to the other, the direction being chosen so as to give the lowest number possible to the position of the phenyl group.

The standard process used by the petrochemical industry for producing BAB consists of oligomerizing light olefins, particularly propylene, to branched olefins having 10 to 14 carbon atoms and then alkylating benzene with the branched olefins in the presence of a catalyst such as HF. Although the product BAB comprises a large number of alkyl-phenyl-alkanes having the general formula $(m_i\text{-alkyl}_i)_i$-n-phenyl-alkane, for the purpose of illustrating three important characteristics of BAB it is sufficient to point out only two examples of BAB: m-alkyl-m-alkyl-n-phenyl-alkanes where m≠n, and m-alkyl-m-phenyl-alkanes where m≧2.

The most prominent characteristic of BAB is that, for a large proportion of BAB, there is attached to the aliphatic alkyl chain of BAB generally at least one alkyl group branch, and more commonly three or more alkyl group branches. BAB thus has a relatively large number of primary carbon atoms per aliphatic alkyl group, since the number of primary carbon atoms per aliphatic alkyl group in BAB equals the number of alkyl group branches per aliphatic alkyl group plus either one if n=1, or two if n≧2, provided that the alkyl group branches themselves are unbranched. If any alkyl group branch itself is branched, then the aliphatic alkyl group in BAB has even more primary carbon atoms. Thus the aliphatic alkyl group in BAB usually has three, four, or more primary carbon atoms. As for the alkyl group branches of the aliphatic alkylation group in BAB, each alkyl group branch is usually a methyl group branch, although ethyl, propyl, or higher alkyl group branches are possible.

Another characteristic of BAB is that the phenyl group in BAB can be attached to any non-primary carbon atom of the aliphatic alkyl chain. This is typical of BAB that is produced from the standard BAB process used by the petrochemical industry. Except for 1-phenyl-alkanes whose formation is known to be disfavored due to the relative instability of the primary carbenium ion and neglecting the relatively minor effect of the branches of the branched paraffins, the oligomerization step produces a carbon-carbon double bond that is randomly distributed along the length of the aliphatic alkyl chain, and the alkylation step nearly randomly attaches the phenyl group to a carbon along the aliphatic alkyl chain. Thus, for example, for a phenyl-alkane which has an aliphatic alkyl chain having 10 carbon atoms and which was produced by the standard BAB process, the phenyl-alkane product would be expected to be an approximately random distribution of 2-, 3-, 4-, and 5-phenyl-alkanes, and the selectivity of the process to a phenyl-alkane like 2-phenyl alkane would be 25 if the distribution was perfectly random, but is typically between about 10 and about 40.

A third characteristic of BAB is the relatively high probability that one of the carbons of the aliphatic alkyl group is a quaternary carbon. In BAB, the quaternary carbon may be, as illustrated by the first BAB example, a carbon in the aliphatic alkyl group other than the carbon that is bonded by a carbon-carbon bond to a carbon in the phenyl group. However, as is illustrated by the BAB second example, the quaternary carbon may also be the carbon that is bonded by a carbon-carbon bond to a carbon in the phenyl group. When a carbon atom on the alkyl side chain not only is attached to two other carbons on the alkyl side chain and to a carbon atom of an alkyl group branch but also is attached to a carbon atom of the phenyl group, the resulting alkyl-phenyl-alkane is referred to as a "quaternary alkyl-phenyl-alkane" or simply a "quat." Thus, quats comprise alkyl-phenyl-alkanes having the general formula m-alkyl-m-phenyl-alkane. If the quaternary carbon is the second carbon atom numbered from an end of the alky side chain, the resulting 2-alkyl-2-phenyl-alkane is referred to as an "end quat." If the quaternary carbon is any other carbon atom of the alkyl side chain, as in the second BAB example, then the resulting alkyl-phenyl-alkane is referred to as an "internal quat." In known processes for producing BAB, a relatively high proportion, typically greater than 10 mol-%, of the BAB is internal quats.

About thirty years ago it became apparent that household laundry detergents made of BABS were gradually polluting rivers and lakes. Investigation into the problem led to the recognition that BABS were slow to biodegrade. Solution of the problem led to the manufacture of detergents made of linear alkylbenzene sulfonates (LABS), which were found to biodegrade more rapidly than BABS. Today, detergents made of LABS are manufactured world-wide. LABS are manufactured from another type of alkylbenzenes called linear alkylbenzenes (LAB). The standard process used by the petrochemical industry for producing LAB consists of dehydrogenating linear paraffins to linear olefins and then alkylating benzene with the linear olefins in the presence of a catalyst such as HF or a solid catalyst. LAB are phenyl-alkanes comprising a linear aliphatic alkyl group and a phenyl group and have the general formula n-phenyl-alkane. LAB has no alkyl group branches, and consequently the linear aliphatic alkyl group normally has two primary carbon atoms (i.e., n≧2). Another characteristic of LAB that is produced by the standard LAB process is that the phenyl group in LAB is usually attached to any secondary carbon atom of the linear aliphatic alkyl group. In LAB produced using HF catalyst the phenyl group is slightly more likely to attach to a secondary carbon near the center as opposed to near the end of the linear aliphatic alkyl group, while in LAB produced by the Detal™ process approximately 25–35 mol-% of n-phenyl-alkanes are 2-phenyl-alkanes.

Over the last few years, other research has identified certain modified alkylbenzene sulfonates, which are referred to herein as MABS, which are different in composition from all alkylbenzene sulfonates used currently in commerce, including BABS and LABS, and from all alkylbenzene sulfonates produced by prior alkylbenzene processes, including those which alkylate aromatics using catalysts such as HF, aluminum chloride, silica-alumina, fluorided silica-alumina, zeolites, and fluorided zeolites. MABS also differ from these other alkylbenzene sulfonates by having improved laundry cleaning performance, hard surface cleaning performance, and excellent efficiency in hard water, while also having biodegradability comparable to that of LABS.

MABS can be produced by sulfonating a third type of alkylbenzenes called modified alkylbenzenes (MAB), and the desired characteristics of MAB are determined by the desired solubility, surfactancy, and biodegradability properties of MABS. MAB is a phenyl-alkane comprising a lightly branched aliphatic alkyl group and a phenyl group and has the general formula $(m_i-alkyl_j)_i$-n-phenyl-alkane. MAB usually has only one alkyl group branch, and the alkyl group branch is a methyl group, which is preferred, an ethyl group, or an n-propyl group, so that, where there is only one alkyl group branch and n≠1, the aliphatic alkyl group in MAB has three primary carbons. However, the aliphatic alkyl group in MAB may have two primary carbon atoms if there is only one alkyl group branch and n=1, or, if there are two alkyl group branches and n≠1, four primary carbons. Thus, the first characteristic of MAB is that the number of primary carbons in the aliphatic alkyl group in MAB is intermediate between that in BAB and that in LAB. Another characteristics of MAB is that it contains a high proportion of 2-phenyl-alkanes, namely that from about 40 to about 100% of phenyl groups are attached selectively to the second carbon atom as numbered from an end of the alkyl side chain.

A final characteristic of the MAB alkylate is that the MAB has a relatively low proportion of internal quats. Some internal quats such as 5-methyl-5-phenyl-undecane produce MABS that has shown slower biodegradation, but end quats such as 2-methyl-2-phenyl-undecane produce MABS that show biodegradation similar to that of LABS. For example, biodegradation experiments show that in a porous pot activated sludge treatment, the ultimate biodegradation was greater for sodium 2-methyl-2-undecyl [$C^{14}$] benzenesulfonate than for 5-methyl-5-undecyl [$C^{14}$] benzenesulfonate. See the article entitled "Biodegradation of Coproducts of Commercial Linear Alkylbenzene Sulfonate," by A. M. Nielsen et al., in Environmental Science and Technology, Vol. 31, No. 12, 3397–3404 (1997). A relatively low proportion, typically less than 10 mol-%, of the MAB is internal quats.

Because of the advantages of MABS over other alkylbenzene sulfonates, catalysts and processes are sought that selectively produce MAB. As suggested by the foregoing, two of the chief criteria for an alkylation process for the production of MAB are selectivity to 2-phenyl-alkanes and selectivity to internal quaternary phenyl-alkanes. Prior art alkylation processes for the production of LAB using catalysts such as aluminum chloride or HF are believed to be incapable of producing MAB having the desired 2-phenyl-alkane selectivity and internal quat selectivity. In these prior art processes, when lightly branched olefins (i.e., olefins that have essentially the same light branching as that of the aliphatic alkyl group of MAB) react with benzene, quaternary phenyl-alkanes selectively form. One reaction mechanism that accounts for such selective quaternary phenyl-alkane formation is that the delinearized olefins convert, to various extents, into primary, secondary, and tertiary carbenium ion intermediates. Of these three carbenium ions, tertiary carbenium ions are the most stable, and because of their stability, are the most likely to form and react with benzene, thus forming a quaternary phenyl-alkane. Although alkylation processes using catalysts including mordenite, ZSM-4, ZSM-12, ZSM-20, offretite, gmelinite, and beta zeolite have been proposed for the production of MAB, catalysts and processes continue to be sought that will satisfy the expected marketplace demands and commercial quality standards for MABS.

SUMMARY OF THE INVENTION

In its broadest embodiment, this invention is a process for producing an arylalkane, where the process comprises contacting monoolefin molecules having from about 8 to about 28 carbon atoms with an aryl compound at alkylation conditions with a zeolite having an NES zeolite structure type. Unlike prior art processes for the production of detergent-range alkylbenzenes generally, including linear (LAB) and modified (MAB), this broadest embodiment of the present invention uses a zeolite having an NES zeolite structure type as an alkylation catalyst.

In a broad embodiment that relates more specifically to the production of modified alkylbenzenes (MAB), this invention is a process for the production of arylalkanes by contacting $C_8$ to $C_{28}$ monoolefins, which have three or four primary carbon atoms and no quaternary carbon atoms, with aryl compounds in the presence of a zeolite having an NES zeolite structure type. Examples of NES zeolites include NU-87 and gottardiite. The arylalkanes have one aryl portion and one $C_8$ to $C_{28}$ aliphatic alkyl portion. Of the carbon atoms of the aliphatic alkyl portion, 2, 3, or 4 carbon atoms are primary carbon atoms. None of the carbon atoms of the aliphatic alkyl portion is a quaternary carbon atom except for any quaternary carbon atom bonded by a carbon-carbon bond with a carbon atom of the aryl portion. This embodiment of the invention has a selectivity to 2-phenyl-alkanes of from 40 to 100 and a selectivity to internal quaternary phenyl-alkanes of less than 10. This embodiment of this invention, when used for detergent alkylation, meets the increasingly stringent requirements of 2-phenyl-alkanes selectivity and internal quaternary phenyl-alkane selectivity for the production of modified alkylbenzenes (MAB). Without being bound by any particular theory, it is believed that the shape of the pores and channels of NES zeolites are particularly well-suited for selectively producing the desired modified linear alkylbenzene (MAB) isomers, because they selectively inhibit the formation of transition states leading to the production of quaternary phenyl-alkanes. Thus, it is believed that zeolites having an NES zeolite structure type are shape-selective for the production of MAB. This invention is useful in the production MAB, which can in turn be sulfonated to produce modified linear alkylbenzene sulfonates (MABS), which have improved cleaning effectiveness in hard and/or cold water while also having biodegradability comparable to that of linear alkylbenzene sulfonates.

Additional embodiments are described in the following description of this invention.

INFORMATION DISCLOSURE

LAB processes are described in the book edited by Robert A. Meyers entitled *Handbook of Petroleum Refining Processes*, (McGraw-Hill, New York, Second Edition, 1997) at pages 1.53 to 1.66, the teachings of which are incorporated herein by reference. Paraffin dehydrogenation processes are described in the Meyers book at pages 5.11 to 5.19, the teachings of which are incorporated herein by reference.

NU-87 is described at pages 162–163 in *Atlas of Zeolite Structure Types*, by W. M. Meier, et al., published on behalf of the Structure Commission of the International Zeolite Association by Elsevier, Boston, Mass., USA, Fourth Revised Edition, 1996. The teachings of the *Atlas of Zeolite Structure Types*, Fourth Revised Edition, respecting the NES structure type and NU-87 are incorporated herein by reference. NU-87 is also described in U.S. Pat. No. 5,102,641 (Casci et al.), the teachings of which are incorporated herein by reference, and in the article entitled "Structure of the two-dimensional medium-pore high-silica zeolite NU-87," by M. D. Shannon et al., in Nature, Vol. 353, 417–420 (Oct. 3, 1991), the teachings of which are incorporated herein by reference.

Gottardiite, which has an isotypic framework structure of the NES zeolite structure type, is described in the articles entitled "The crystal structure of gottardiite, a new natural zeolite," by A. Alberti et al., in Eur. J. Mineral., 8, 69–75 (1996), and "Gottardiite, a new high-silica zeolite from Antarctica: the natural counterpart of synthetic NU-87," by E. Galli et al., in Eur. J. Mineral., 8, 687–693 (1996). The teachings of these two articles on gottardiite are incorporated herein by reference.

Alkylation of benzene with a $C_2$ olefin (ethylene) to produce ethylbenzene using catalysts comprising NU-87 is described in U.S. Pat. No. 5,041,402 (Casci et al.). U.S. Pat. No. 5,041,402 (Casci et al.) describes other alkylations using methanol and ethers, and mentions other alkylated products including methyltoluene, ethyltoluene, and cumene. Similar alkylations using catalysts comprising NU-85, which is an intergrowth of zeolites EU-1 and NU-87, are described in U.S. Pat. No. 5,446,234 (Casci et al.)

DETAILED DESCRIPTION OF THE INVENTION

The broadest embodiment of this invention is directed to the production of phenyl-alkanes for detergent-range alkylbenzenes generally, including branched (BAB), linear (LAB), or modified (MAB) alkylbenzenes. In this broadest embodiment, the monoolefin may be a highly branched monoolefin or a linear (unbranched) olefin, but, especially for the production of MAB, the monoolefin is preferably a lightly branched monoolefin. A lightly branched monoolefin, as used herein, refers to a monoolefin having a total number of carbon atoms of from about 8 to about 28, of which three or four of the carbon atoms are primary carbon atoms and none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. Preferably, the lightly branched monoolefin has a total number of from 8 to 15 carbon atoms, and more preferably from 10 to 15 carbon atoms.

The lightly branched monoolefin generally comprises an aliphatic alkene having the general formula of $(p_i\text{-alkyl}_i)_i$-q-alkene. The lightly branched monoolefin consists of an aliphatic alkenyl chain, which is referred to by "alkene" in the $(p_i\text{-alkyl}_i)_i$-q-alkene formula, and is the longest straight chain containing the carbon-carbon double bond of the lightly branched monoolefin. The lightly branched monoolefin also consists of one or more alkyl group branches, each of which is attached to the aliphatic alkenyl chain and is designated by a corresponding "$(p_i\text{-alkyl}_i)$" in the $(p_i\text{-alkyl}_i)_i$-q-alkene formula. If it is possible to select two or more chains of equal lengths as the aliphatic alkenyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $p_i$ of the aliphatic alkenyl chain. The double bond is between carbon number q and carbon number (q+1) of the aliphatic alkenyl chain. The aliphatic alkenyl chain is numbered from one end to the other, the direction being chosen so as to give the lowest number possible to the carbon atoms bearing the double bond.

The lightly branched monoolefin may be an alpha monoolefin or a vinylidene monoolefin, but is preferably an internal monoolefin. As used herein, the term "alpha olefins" refers to olefins having the chemical formula, R—CH=CH$_2$. The term "internal olefins," as used herein, includes di-substituted internal olefins having the chemical formula R—CH=CH—R; tri-substituted internal olefins having the chemical formula R—C(R)=CH—R; and tetra-substituted olefins having the chemical formula R—C(R)=C(R)—R. The di-substituted internal olefins include beta internal olefins having the chemical formula R—CH=CH—CH$_3$. As used herein, the term "vinylidene olefins" refers to olefins having the chemical formula R—C(R)=CH$_2$. In each of the preceding chemical formulas in this paragraph, R is an alkyl group that may be identical to or different from other alkyl group(s), if any, in each formula. Insofar as permitted by the definition of the term "internal olefin", when the lightly branched monoolefin is an internal monoolefin, any two carbon atoms of the aliphatic alkenyl chain may bear the double bond. Suitable lightly branched monoolefins include octenes, nonenes, decenes, undecenes, dodecenes, tridecenes, tetradecenes, pentadecenes, hexadecenes, heptadecenes, octadecenes, nonadecenes, eicosenes, heneicosenes, docosenes, tricosenes, tetracosenes, pentacosenes, hexacosenes, heptacosenes, and octacosenes.

The alkyl group branch or branches of the lightly branched monoolefin are generally selected from methyl, ethyl, and propyl groups, with shorter and normal branches being preferred. Preferably, the lightly branched monoolefin has only one alkyl group branch, but two alkyl group branches are also possible. Lightly branched monoolefins having either two alkyl group branches or four primary carbon atoms comprise generally less than 40 mol-%, and preferably less than about 25 mol-%, of the total lightly branched monoolefins. Lightly branched monoolefins having either one alkyl group branch or three primary carbon atoms comprise preferably more than 70 mol-% of the total lightly branched monoolefins. Any alkyl group branch can be bonded to any carbon on the aliphatic alkenyl chain.

The composition of a mixture of lightly branched monoolefins can be determined by analytical methods that are well-known to a person of ordinary skill in the art of gas chromatography and need not be described here in detail. The article written by H. Schulz, et al. and published starting at page 315 of the Chromatographia 1, 1968, which is incorporated herein by reference, describes a temperature-programmed gas chromatograph apparatus and method that is suitable for identifying components in complex mixtures of paraffins. A person of ordinary skill in the art can modify the apparatus and method in the article by Schulz et al. to equip the injector with a hydrogenator insert tube in order to hydrogenate the lightly branched monoolefins to lightly branched paraffins in the injector. The lightly branched paraffins are then separated and identified using essentially the apparatus and method described in the article by Schulz et al.

In addition to the lightly branched monoolefin, other acyclic compounds may contact the zeolite having an NES zeolite structure type. These other acyclic compounds may be brought into contact with the zeolite either via a stream containing one or more lightly branched monoolefins, which is referred to herein as the olefinic feedstock, or via one or more other streams. Other acyclic compounds include non-branched (linear) olefins and nonolefins, including linear and nonlinear paraffins. Nonbranched (linear) olefins which may contact the zeolite have a total number of carbon atoms per paraffin molecule of generally from about 8 to about 28, preferably from 8 to 15, and more preferably from 10 to 14 carbon atoms. Two carbon atoms per nonbranched olefin molecule are primary carbon atoms and the remaining carbon atoms are secondary carbon atoms. A secondary carbon atom is a carbon atom which, although possibly bonded also to other atoms besides carbon, is bonded to only two carbon atoms. The nonbranched olefin may be an alpha monoolefin but is preferably an internal monoolefin. To the extent allowed by the definition of the term "internal olefin", when the nonbranched monoolefin is an internal monoolefin, any two carbon atoms of the aliphatic alkenyl chain may bear the double bond. When present in the olefinic feedstock with the lightly branched monoolefins, the linear olefin content may be as high as, or no more than, about 75 mol-% of the total monoolefins in the olefinic feedstock, but is generally less than about 40 mol-% of the total monoolefins in the olefinic feedstock.

Because of the possible presence in the olefinic feedstock of linear monoolefins, in addition to the lightly branched monoolefins, the bulk olefinic feedstock may contain, on average, fewer than 3, or between 3 and 4, primary carbon atoms per monoolefin molecule in the olefinic feedstock. Depending on the relative proportions of linear and lightly branched monoolefins, the olefinic feedstock, or the sum of all the monoolefins that contact the zeolite, may have from 2.25 to 4 primary carbon atoms per monoolefin molecule.

Linear and/or nonlinear paraffins, if any, which may contact the zeolite, via the olefinic feedstock or not, have a total number of carbon atoms per paraffin molecule of generally from about 8 to about 28, preferably from 8 to 15, and more preferably from 10 to 14 carbon atoms. Such linear and nonlinear paraffins are expected to act as a diluent in the alkylation step and not to materially interfere with the alkylation step. However, the presence of such diluents in the alkylation reactor generally results in higher volumetric flow rates of process streams, and, in order to accommodate these higher flow rates, larger equipment in the alkylation reaction circuit (i.e., larger alkylation reactor and more alkylation catalyst), and larger product recovery facilities may be required. Preferably, the olefinic feedstock does not contain unacceptable concentrations of impurities or poisons which would cause difficulties in the alkylation step. Some impurities can be removed by well-known steps, such as distillation to remove lower-boiling and higher-boiling undesired materials and selective hydrogenation to convert polyolefins, such as diolefins, to monoolefins. When the product of the alkylation step is a specific phenyl-alkane that results from monoalkylating an aryl compound with a particular lightly branched olefin, the olefinic feedstock preferably contains little, and more preferably none, of the dimer of that particular lightly branched olefin.

Monoolefins that are more highly branched than the lightly branched monoolefins may also be present in the olefinic feedstock, but because on alkylation such highly branched monoolefins tend to form BAB, preferably their concentration in the olefinic feedstock is minimized. For example, the olefinic feedstock may contain monoolefin molecules consisting of at least one quaternary carbon atom, which tend on alkylation to form phenyl-alkanes that have in the aliphatic alkyl portion a quaternary carbon atom that is not bonded by a carbon-carbon bond with a carbon atom of the aryl portion. Therefore, monoolefin molecules consisting of at least one quaternary carbon atom preferably comprise less than 1% of the olefinic feedstock or of the sum of all the monoolefins that contact the zeolite.

The lightly branched monoolefins, or the olefinic feedstock, may come from a number of sources. Lightly branched monoolefins can be produced by first isomerizing normal paraffins to lightly branched paraffins, that is, to paraffins that have essentially the same light branching as that desired of the aliphatic alkyl group of MAB, and then dehydrogenating the lightly branched paraffins to lightly branched monoolefins. It is not necessary, of course, that the paraffins that are isomerized be normal paraffins, for all that is required is that the paraffins that are isomerized have less light branching than that desired in the aliphatic alkyl group of MAB. Alternatively, lightly branched monoolefins can be produced by first generating monoolefins by well-known processes such as ethylene oligomerization, derivation from cracked wax, or Fischer-Tropsch synthesis. Monoolefins produced by these processes generally have less light branching than what is desired for the aliphatic alkyl group of MAB, and consequently these monoolefins are subsequently isomerized to produce the lightly branched monoolefins. In another alternative, lightly branched paraffins can be separated or otherwise recovered from straight-run kerosene by separation processes including adsorptive separation and/or distillation, and then dehydrogenated to lightly branched monoolefins. Yet another method for producing lightly branched monoolefins is first to dehydrogenate normal paraffins to normal monoolefins, and then to isomerize the normal monoolefins to lightly branched monoolefins. The discussion herein of the production or provision of lightly branched monoolefins for this invention will be in reference to this last method, but it is not intended that this discussion limit the scope of the present invention as set forth in the claims.

Processes for the dehydrogenation of normal paraffins are well-known to persons of ordinary skill in the art of hydrocarbon processing and need not be described in detail herein. Briefly, a feed stream containing paraffins combines with make-up and recycled hydrogen and recycled unreacted paraffins to form a reactant stream that is heated and passed though a bed of a suitable catalyst maintained at the proper dehydrogenation conditions of temperature, pressure, etc. The effluent of this catalyst bed, that is the dehydrogenation reactor effluent stream, is usually cooled, partially condensed, and passed to a vapor-liquid or product separator. The condensed material, which is herein called the dehydrogenated product stream, passes to a stripping separation zone, which usually includes a stripping column that removes all compounds which are more volatile than the lightest hydrocarbon which is desired to be isomerized. See the book edited by Robert A. Meyers entitled *Handbook of Petroleum Refining Processes*, (McGraw-Hill, New York, Second Edition, 1997) at pages 5.11 to 5.19, and U.S. Pat. No. 5,276,231, which describes a process for the selective removal of aromatic by-products from dehydrogenation processes. The teachings of U.S. Pat. No. 5,276,231, which also teaches the selective hydrogenation of diolefinic byproducts from dehydrogenation, are incorporated herein by reference. The dehydrogenated product stream—as opposed to the effluent of the stripping separation zone—can usually be isomerized directly to make the lightly branched monoolefins, provided that the dehydrogenation reaction is usually not run to the thermodynamic limitation in order to minimize cracking and other undesirable and deleterious by-products including dimethyl olefins in the dehydrogenated product stream. The polyolefin by-products formed during dehydrogenation are preferably minimized. The monoolefin-containing stream from the paraffin dehydrogenation process is typically a mixture largely of unreacted paraffins, from about 20 to about 80 vol-% of linear (unbranched) olefins, and branched monoolefins which typically are in the $C_8$–$C_{28}$ range, although those in the $C_8$–$C_{15}$ range are preferred in the practice of this invention, and those in the $C_{10}$–$C_{15}$ range are even more preferred. Unsaturation may appear anywhere on the chain of the substantially linear monoolefin.

The linear monoolefins in the dehydrogenation reaction effluent are passed to a skeletal isomerization step, which sufficiently decreases the linearity of the dehydrogenation reaction effluent so that, after use in alkylation in accord with this invention, the phenyl-alkane alkylate meets the requirements for primary carbon atoms, 2-phenyl-alkane selectivity, and internal quaternary phenyl-alkane selectivity. Skeletal isomerization of the starting-material olefins can be accomplished in any manner known in the art or by using any catalyst known in the art. Suitable catalysts include ferrierite, ALPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MeAPSO-11, MeAPSO-31, MeAPSO-41, MeAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite. Many natural zeolites, such as ferrierite, that have an initially reduced pore size can be converted to forms suitable for olefin skeletal isomerization by removing associated alkali metal or alkaline earth metal by ammonium ion exchange and calcination to produce the substantially hydrogen form, as taught in U.S. Pat. Nos. 4,795,623 and 4,924,027. However, H-form mordenite is not a suitable catalyst for skeletal isomerization of the olefinic starting-material. Catalysts and conditions for skeletal isomerization of the olefinic starting-material are disclosed in U.S. Pat. No. 5,510,306 (Murray), U.S. Pat. No. 5,082,956 (Monnier et al.), and U.S. Pat. No. 5,741,759 (Gee et al.). The skeletal isomerization conditions include conditions under which at least a portion, and preferably all, of the hydrocarbons that contact the skeletal isomerization catalyst contact the skeletal isomerization catalyst in the liquid phase.

The product of the skeletal isomerization step contains the lightly branched monoolefins and may be used as the olefinic feedstock. Accordingly, the olefinic feedstock may be a mixture largely of unreacted paraffins, linear (unbranched) olefins, and branched monoolefins which typically are in the $C_8$–$C_{28}$ range, although those in the $C_8$–$C_{15}$ range are preferred in the practice of this invention, and those in the $C_{10}$–$C_{15}$ range are even more preferred. About 20 to about 40 vol-% of the total monoolefins in the olefinic feedstock are linear (unbranched) olefins. The monoalkyl branched olefins in the olefinic feedstock are preferably monomethyl branched olefins. The dialkyl branched olefin content of the olefinic feedstock generally is less than about 30 mol-%, usually between about 10 mol-% and about 20 mol-%, and preferably less than about 10 mol-%, of the olefinic feedstock. The olefinic feedstock can be formed from a portion or an aliquot portion of the product of the skeletal isomerization step. An aliquot portion of the product of the skeletal isomerization step is a fraction of the product of the skeletal isomerization step that has essentially the same composition as the product of the skeletal isomerization step.

The lightly branched monoolefins are reacted with an aryl compound, which is benzene when the process is detergent alkylation. In a more general case, the lightly branched monoolefins could be reacted with other aryl compounds, such as alkylated or otherwise substituted derivatives of benzene including toluene and ethylbenzene, but the product of such an alkylation may not be as suitable a detergent precursor as alkylated benzenes. Although the stoichiometry of the alkylation reaction requires only 1 molar proportion of aryl compound per mole of total monoolefins, the use of a 1:1 mole proportion results in excessive olefin polymerization and polyalkylation. That is, the reaction product under such conditions would consist not only of the desired monoalkylbenzenes, but also of large amounts of the dialkylbenzenes, trialkylbenzenes, possibly higher polyalkylated benzenes, olefin dimers, trimers, etc., and unreacted benzene. On the other hand, it is desired to have the aryl compound:monoolefin molar ratio as close to 1:1 as possible to maximize utilization of the aryl compound and to minimize the recycle of unreacted aryl compound. The actual molar proportion of aryl compound to total monoolefin will therefore have an important effect on both conversion and, perhaps more importantly, selectivity of the alkylation reaction. In order to carry out alkylation with the conversion and selectivity required using the catalysts of this invention's process, the total aryl compound: monoolefin molar ratio may be generally from about 5:1 up to about 50:1 and normally from about 8:1 to about 35:1.

The aryl compound and the lightly branched monoolefin are reacted under alkylation conditions in the presence of a solid alkylation catalyst comprising a zeolite having an NES zeolite structure type. These alkylation conditions include a temperature in the range between about 176° F. (80° C.) and about 392° F. (200° C.), most usually at a temperature not exceeding 347° F. (175° C.). Since the alkylation is conducted in at least partial liquid phase, and preferably in either an all-liquid phase or at supercritical conditions, pressures for this embodiment must be sufficient to maintain reactants in the liquid phase. The requisite pressure necessarily depends upon the olefin, the aryl compound, and temperature, but normally is in the range of 200–1000 psi(g) (1379–6895 kPa(g)), and most usually 300–500 psi(g) (2069–3448 kPa(g)).

While the alkylation conditions are sufficient to alkylate the aryl compound with the lightly branched monoolefin, it is believed that under alkylation conditions only minimal skeletal isomerization of the lightly branched monoolefin occurs. As used herein, skeletal isomerization of an olefin under alkylation conditions means isomerization that occurs during alkylation and which changes the number of carbon atoms in the aliphatic alkenyl chain of the olefin, in the aliphatic alkyl chain of the phenyl-alkane product, or in any reaction intermediate that is formed or derived from the lightly branched monoolefin prior to the withdrawal of the phenyl-alkane product from the alkylation conditions. By minimal skeletal isomerization it is meant that generally less than 15 mol-%, and preferably less than 10 mol-%, of the olefin, the aliphatic alkyl chain, and any reaction intermediate undergoes skeletal isomerization. It is further believed that under alkylation conditions minimal skeletal isomerization occurs for any other olefins in the olefinic feedstock. Thus, alkylation preferably occurs in the substantial absence of skeletal isomerization of the lightly branched monoolefin, and the extent of light branching of the lightly branched monoolefin is identical to the extent of light branching in the aliphatic alkyl chain in the phenyl-alkane product molecule. Accordingly, the number of primary carbon atoms in the lightly branched monoolefin is preferably the same as the number of primary carbon atoms per phenyl-alkane molecule. Insofar as an additional methyl group branch does form on the aliphatic alkyl chain of the phenyl-alkane product, the number of primary carbon atoms in the phenyl-alkane product may be slightly higher the number of primary carbon atoms in the lightly branched monoolefin. Finally, although the formation of 1-phenyl-alkane product is not significant at alkylation conditions, insofar as a 1-phenyl-alkane molecule is formed by alkylating an aryl compound with a lightly branched monoolefin having a primary carbon atom on each end of the aliphatic alkenyl chain, the number of primary carbon atoms in the phenyl-alkane product will be slightly less than the number of primary carbon atoms in the lightly branched monoolefin.

According to the broad embodiment of this invention, the alkylation of the aryl compound with the lightly branched monoolefins produces $(m_i\text{-alkyl}_i)_i$-n-phenyl-alkanes, where the aliphatic alkyl group has two, three, or four primary carbon atoms per phenyl-alkane molecule. Preferably, the aliphatic alkyl group has three primary carbon atoms per phenyl-alkane molecule, and more preferably one of the three primary carbon atoms is in a methyl group at one end of the aliphatic alkyl chain, the second primary carbon atom is in a methyl group at the other end of the chain, and the third primary carbon atom is in a single methyl group branch attached to the chain. However, it is not necessary that all of the $(m_i\text{-alkyl}_i)_i$-n-phenyl-alkanes produced by the present invention have the same number of primary carbon atoms per phenyl-alkane molecule. Generally from about 0 mol-% to about 75 mol-%, and preferably from about 0 mol-% to about 40 mol-%, of the $(m_i\text{-alkyl}_i)_i$-n-phenyl-alkanes produced may have 2 primary carbon atoms per phenyl-alkane molecule. Generally, as many as possible, and typically from about 25 mol-% to about 100 mol-%, of the $(m_i\text{-alkyl}_i)_i$-n-phenyl-alkanes produced may have 3 primary carbon atoms per phenyl-alkane molecule. Generally from about 0 mol-% to about 40 mol-% of the $(m_i\text{-alkyl}_i)_i$-n-phenyl-alkanes produced may have 4 primary carbon atoms. It is expected that the number of primary, secondary, and tertiary carbon atoms per product arylalkane molecule can be determined by high resolution multipulse NMR spectrum editing and distortionless enhancement by polarization transfer (DEPT), which is described in the brochure entitled "High Resolution Multipulse NMR Spectrum Editing and DEPT," which is distributed by Bruker Instruments, Inc., Manning Park, Billerica, Mass., USA, and which is incorporated herein by reference.

The alkylation of the aryl compound with the lightly branched monoolefins in accord with the broad embodiment of this invention has a selectivity of 2-phenyl-alkanes of generally from about 40 to about 100 and preferably from about 60 to about 100, and an internal quaternary phenyl-alkane selectivity of generally less than 10 and preferably less than 5. Quaternary phenyl-alkanes can form by alkylating the aryl compound with a lightly branched monoolefin having at least one tertiary carbon atom. A tertiary carbon atom is a carbon atom which, while also possibly bonded to other atoms besides carbon, is bonded to only three carbon atoms. If, on alkylation, a tertiary carbon atom of the monoolefin forms a carbon-carbon bond with one of the carbon atoms of the aryl compound, that tertiary carbon atom becomes a quaternary carbon atom of the aliphatic alkyl chain. Depending on the location of the quaternary carbon atom with respect to the ends of the aliphatic alkyl chain, the resulting quaternary phenyl-alkane may be either an internal or an end quat.

Alkylation of the aryl compound by the lightly branched monoolefins in accord with this invention may be conducted either as a batch method or in a continuous manner, although the latter is greatly preferred and therefore will be described in some detail. The composites of this invention used as catalyst may be used as a packed bed or a fluidized bed. The olefinic feedstock to the reaction zone may be passed either upflow or downflow, or even horizontally as in a radial bed reactor. The admixture of benzene and the olefinic feedstock containing the lightly branched monoolefins is introduced at a total aryl compound:monoolefin molar ratio of between 5:1 and 50:1, although usually the molar ratio is in the range between about 8:1 and 35:1. In one desirable variant, olefin may be fed into several discrete points within the reaction zone, and at each zone the aryl compound:monoolefin molar ratio may be greater than 50:1. However, the total benzene:olefin ratio used in the foregoing variant of this invention still will be within the stated range. The total feed mixture, that is, aryl compound plus olefinic feedstock containing lightly branched monoolefins, is passed through the packed bed at a liquid hourly space velocity (LHSV) between about 0.3 and about 6 hr$^{-1}$ depending upon alkylation temperature, how long the catalyst has been used, and so on. As used herein, the term "liquid hourly space velocity" means the volumetric flow rate of liquid per hour divided by the catalyst volume, where the liquid volume and the catalyst volume are in the same volumetric units. The temperature in the reaction zone will be maintained at between about 80° C. and about 200° C. (176 to 392° F.), and pressures generally will vary between about 200 and about 1000 psi(g) (1379 to 6895 kPa(g)) to ensure a liquid phase or supercritical conditions.

The class of catalysts which may be used in the practice of this invention comprise zeolites having an NES zeolite structure type, including isotypic framework structures such as NU-87 and gottardiite. The NES zeolite structure type, the term "zeolite structure type," and the term "isotypic framework structure" are used herein as they are defined and used in the previously mentioned *Atlas of Zeolite Structure Types*, Fourth Revised Edition. NU-87 is a two-dimensional medium-pore, high silica, 10-ring channel zeolite having a major pore dimension of 4.7×6.0 Angstroms. Without being bound by any particular theory, it is believed that the pores characterizing zeolites that are useful in the present alkylation process are somewhat elliptical, as opposed to substantially circular. Furthermore, the zeolites useful in this invention have a major pore dimension intermediate between that of the relatively large pore zeolites, such as the X and Y zeolites, and the relatively small pore zeolites, such as ZSM-5 and ZSM-11. Preferably, the major pore dimension is between about 4.5 and 6.5 Angstroms. Any alkylation catalyst comprising a zeolite having an NES zeolite structure type may be used in the present invention, provided that the requirements for conversion, selectivity, and activity are met.

Useful zeolites for the present invention generally have at least 10 percent of the cationic sites thereof occupied by ions other than alkali or alkaline-earth metals. Such other ions include, but are not limited to hydrogen, ammonium, aluminum, rare earth, zinc, copper, and aluminum. Of this group, particular preference is accorded ammonium, hydrogen, rare earth, or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. In certain embodiments, the extent of replacement is such as to produce a zeolite material in which at least 50 percent of the cationic sites are occupied by hydrogen ions.

The zeolites may be subjected to various chemical treatments, including alumina extraction (dealumination) and combination with one or more metal components, such as the metals of Groups IIIB (IUPAC 3), IVB (IUPAC 4), VIB (IUPAC 6), VIIB (IUPAC 7), VIII (IUPAC 8–10), and IIB (IUPAC 12). It is also contemplated that the zeolites may, in some instances, desirably be subjected to thermal treatment, including steaming or calcination in air, hydrogen, or an inert gas, e.g. nitrogen or helium. A suitable steaming treatment comprises contacting the zeolite with an atmosphere containing from about 5 to about 100% steam at a temperature of from about 250° C. (482° F.) to 1000° C. (1832° F.). Steaming may last for a period of between about 0.25 and about 100 hours and may be conducted at pressures ranging from sub-atmospheric to several hundred atmospheres.

It may be useful to incorporate the zeolites that are useful in this invention in another material, e.g., a matrix material or binder that is resistant to the temperature and other conditions used in the process. Suitable matrix materials include synthetic substances, naturally occurring substances, and inorganic materials such as clay, silica, and/or metal oxides. Matrix materials can be in the form of gels including mixtures of silica and metal oxides. Gels including mixtures of silica and metal oxides may be either naturally occurring or in the form of gels or gelatinous precipitates. Naturally occurring clays which can be composited with the zeolite used in this invention include those of the montmorillonite and kaolin families, which families include the sub-bentonites and the kaolins commonly known as Dixie, McNamee-Georgia, and Florida clays or others in which the main mineral constituent is halloysite, kaolinite, dickite, nacrite, or anauxite. Such clays can be used as a matrix material in their raw states as originally mined, or can be subjected to calcination, acid treatment or chemical modification prior to their use as matrix materials. In addition to the foregoing materials, the zeolite used in this invention may be compounded with a porous matrix material, such as alumina, silica-alumina, silica-magnesia, silica-zirconia, silica-thoria, silica-beryllia, silica-titania, and aluminum phosphate as so well as ternary combinations, such as silica-alumina-thoria, silica-alumina-zirconia, silica-alumina-magnesia, and silica-magnesia-zirconia. The matrix material may be in the form of a cogel. The relative proportions of and matrix material may vary widely, with the zeolite content ranging generally from between about 1 and about 99% by weight, usually in the range of about 5 to about 80% by weight, and preferably in the range of about 30 to about 80% by weight, of the combined weight of zeolite and matrix material.

The zeolites that are useful in this invention generally have a framework silica:alumina molar ratio of from about 10:1 to about 50:1, and more usually from about 20:1 to about 40:1. As used herein, the term "framework silica:alumina molar ratio" means the molar ratio of silica per alumina, that is the molar ratio of $SiO_2$ per $Al_2O_3$, in the zeolite framework. This framework silica:alumina molar ratio may be different from the silica:alumina molar ratio result determined by some physical and chemical methods. For example, a gross chemical analysis may detect aluminum which is present in the form of cations associated with the acidic sites of the zeolite, thereby resulting in a lower silica:alumina ratio than the framework silica:alumina molar ratio. Similarly, if a silica:alumina molar ratio is determined by thermogravimetric analysis (TGA) of ammonia desorption, the quantity of ammonia titrated may be affected by cationic aluminum preventing exchange of the ammonium ions on to the acidic sites. In this case, the silica:alumina molar ratio determined by TGA may be higher than the framework silica:alumina molar ratio. These differences are more likely to arise when the zeolite undergoes treatments, such as dealuminization, which result in ionic aluminum that is free of the zeolite structure being present in the zeolite. For these reasons, care should be used to ensure that the framework silica:alumina molar ratio is measured accurately.

When zeolites having an NES zeolite structure type have been prepared in the presence of organic cations they may not be sufficiently catalytically active for alkylation. Without being bound to any particular theory, it is believed that the insufficient catalytic activity is the result of the organic cations from the forming solution occupying the intracrystalline free space. Such catalysts may be activated, for example, by heating in an inert atmosphere at 540° C. (1004° F.) for one hour, ion exchanging with ammonium salts, and calcining at 540° C. (1004° F.) in air. Although the presence of organic cations in the forming solution may not be essential to forming zeolites having an NES zeolite structure type; their presence appears to favor the formation of the this type of zeolite structure. Some natural zeolites may sometimes be converted to zeolites of the desired type by various activation procedures and other treatments such as ion exchange, steaming, alumina extraction, and calcination. When synthesized in the alkali metal form, the zeolite is conveniently converted to the hydrogen form, generally by intermediate formation of the ammonium form as a result of ammonium ion exchange and calcination of the ammonium form to yield the hydrogen form. Although the hydrogen form of the zeolite catalyzes the reaction successfully, the zeolite may also be partly in the alkali metal form.

The following examples are solely for purposes of illustration. These examples show in detail how the invention claimed below may be effected, and are not meant to limit the scope of this invention to the embodiments shown in the examples. The examples report results for selectivity to 2-phenyl-alkanes.

In the examples, the selectivity to 2-phenyl-alkanes is determined by $^{13}C$ NMR spectroscopy, since $^{13}C$ NMR spectroscopy can distinguish a peak associated with the chemical shift of the benzylic carbon in 2-phenyl-alkanes from those of the benzylic carbon in n-phenyl-alkane where n≠2, regardless of whether the aliphatic alkyl group has alkyl group branches. As used herein, the term "benzylic carbon" means the carbon in the ring of the phenyl group that is attached to the alkyl side chain. The selectivity to 2-phenyl-alkanes can be expressed by the equation:

$$E=R/(R+S)*100,$$

where E equals 2-phenyl-alkane selectivity, R equals the integral of the peak associated with the chemical shift of the benzylic carbon in 2-phenyl-alkanes, with or without alkyl group branches, and S equals the sum of the integrals of the peaks associated with the chemical shifts of the benzylic carbons in each of the n-phenyl-alkanes where n≠2, with or without alkyl group branches.

Also, in the examples, the internal quaternary phenyl-alkane selectivity, which is defined as the selectivity to m-phenyl-m-alkyl-alkanes where m>2, can be determined by $^{13}C$ NMR spectroscopy. An approximate measure of the selectivity to internal quaternary phenyl-alkanes can be expressed by the equation:

$$G=Y/(Y+W)*100,$$

where G equals internal quat selectivity, Y equals the integral of the peak associated with the chemical shift of the benzylic carbon in m-alkyl-m-phenyl-alkanes where m>2, with or without alkyl group branches in addition to the alkyl group branch at carbon m of the aliphatic alkyl chain, and W equals the sum of the integrals of the peaks associated with the chemical shifts of the benzylic carbons in each of 2-alkyl-2-phenyl-alkanes, m-alkyl-n-phenyl-alkanes where m≧2 and m≠n, and n-phenyl-alkanes where n≧1 which have no alkyl group branches. Using $^{13}C$ NMR spectroscopy, it is possible to identify a peak associated with the chemical shift of the benzylic carbon in m-alkyl-m-phenyl-alkanes where m>3 (that is, in all of the internal quats except those where m=3) separately from the peaks associated with the chemical shifts of the benzylic carbons in each of 2-alkyl-2-phenyl-alkanes (that is, end quats), m-alkyl-n-phenyl-alkanes where m≧2 and m≠n (that is, nonlinear nonquats), and in n-phenyl-alkanes (that is, linear nonquats). However, the equation is approximate because of the difficulty when using $^{13}C$ NMR spectroscopy in distinguishing between on the one hand 3-alkyl-3-phenyl-alkanes and on the other hand both m-alkyl-2-phenyl-alkanes where m≧3 and 2-phenyl-alkanes. When 3-alkyl-3-phenyl-alkanes are a small (i.e., less than about 5 mol-%) fraction of all the phenyl-alkanes, the selectivity calculated by this equation is believed to be sufficiently accurate for routine commercial practice.

EXAMPLES

Example 1

Catalyst Preparation

NU-87 was synthesized essentially according to the method of Example 1 of U.S. Pat. No. 5,102,641. The molar ratio of silica:alumina, that is the molar ratio of $SiO_2$ per $Al_2O_3$, of the as-synthesized NU-87 was 47, as determined by gross chemical analysis. The as-synthesized NU-87 was ion-exchanged and calcined essentially according to the method Example 2 of U.S. Pat. No. 5,102,641, except that only one ion exchange was performed. Following the ion-exchange and calcination, the NU-87 had a sodium content of 0.03 wt-%, a Langmuir surface area of 511 m²/g, and a micropore volume of 0.17 cm³/g. The ion-exchanged and calcined NU-87, Catapal B alumina, nitric acid, and water were mixed in a weight ratio of 1:1:0.1:2, respectively, to obtain a mixture. The Catapal B was used as a matrix material or binder. Additional water in the amount of 17 wt-% of the volatile-free solids content of the mixture was added to the mixture in order to achieve a extrudable mixture having a consistency suitable for extruding. The volatile-free solids content of the mixture was determined from the formula:

$$N=1-(L/100),$$

where N equals volatile-free solids content of the mixture and L is the loss on ignition at 900° C. (1652° F.) of the mixture. The extrudable mixture was extruded, dried at 180° C. (356° F.), and calcined at 500° C. (932° F.) for 3 hours, to produce an extrudate.

Example 2

Alkylation

A starting-material of 1-dodecene was isomerized to produce an olefinic feedstock comprising a blend of monomethyl $C_{12}$ olefins and having the composition shown in Table 1.

TABLE 1

| Composition of Olefinic Feedstock | |
|---|---|
| Olefin Component | Content (wt-%) |
| Lights[1] | 0.64 |
| Linear olefins[2] | 30.11 |
| 6-methyl undecene | 7.66 |
| 5-methyl undecene | 15.33 |
| 4-methyl undecene | 11.82 |
| 3-methyl undecene | 12.95 |
| 2-methyl undecene | 8.87 |
| Other alkyl olefins[3] | 9.05 |
| Heavies[4] | 3.53 |
| Total | 99.96 |

[1]Lights include olefins having fewer than 12 carbon atoms.
[2]Linear olefins include $C_{12}$ linear olefins.
[3]Other alkyl olefins include dimethyl, trimethyl, and other $C_{12}$ olefins
[4]Heavies include $C_{12}$ olefin dimers and trimers.

The olefinic feedstock was mixed with benzene to produce a combined feedstock consisting of 93.3 wt-% benzene and 6.7 wt-% olefinic feedstock, which corresponds to a molar ratio of benzene per olefin of about 30:1. A cylindrical reactor, which has a inside diameter of 0.875 in (22.2 mm), was loaded with 75 cc (53.0 g.) of the extrudate prepared in Example 1.

The combined feedstock was passed to the reactor and contacted the extrudate at a LHSV of 2.0 hr$^{-1}$, a total pressure of 500 psi(g) (3447 kPa(g)), and a reactor inlet temperature of 125° C. (257° F.). At these conditions, the reactor lined out over a period of 24 hours and then a first liquid product was collected over the period of the next 6 hours.

After the period of 6 hours of collecting the first liquid product, and with the combined feedstock flowing to the reactor at a LHSV of 2.0 hr$^{-1}$ and a total pressure of 500 psi(g) (3447 kPa(g)), the reactor inlet temperature was increased from 125° C. (257° F.) to 150° C. (302° F.). The reactor lined out over a period of 12 hours with the combined feedstock passing to the reactor and contacting the extrudate at a LHSV of 2.0 hr$^{-1}$, a total pressure of 500 psi(g) (3447 kPa(g)), and a reactor inlet temperature of 150° C. (302° F.). At these conditions, a second liquid product was collected over the period of the next 6 hours.

The second liquid product was analyzed by $^{13}$C NMR in order to determine the contents of 2-phenyl-alkane isomers, internal quaternary phenyl-alkane isomers, and of other phenyl-alkane isomers. The nuclear magnetic resonance analytical method typically consisted of the following. A 0.5 g sample of phenyl-alkane mixture was diluted to 1.5 g with anhydrous deuterated chloroform. A 0.3 milliliter aliquot of the diluted phenyl-alkane mixture was mixed with 0.3 milliliter of 0.1 M chromium (III) acetylacetonate in deuterated chloroform in a 5 mm NMR tube. A small amount of tetramethylsilane (TMS) was added to the mixture as a 0.0 ppm chemical shift reference. The spectrum was run on a Bruker ACP-300 FT-NMR spectrometer, which is available from Bruker Instruments, Inc., Billerica, Mass., USA. The carbon spectrum was run at a field strength of 7.05 Tesla or 75.469 MHz in a 5 mm QNP probe with a sweep width of 22727 Hz (301.1 ppm) and about 65000 data points were collected. The quantitative carbon spectrum was obtained using gated on-acquisition $^{1}$H decoupling (inverse gated decoupling). The quantitative $^{13}$C spectrum was run with 7.99 microsecond (90°) pulses, 1.442 second acquisition time, a 5 second delay between pulses, a decoupler power, using composite pulse decoupling (CPD), of 18H with a pulse width of 105 microseconds (90°) and 2880 scans. The data processing was done with the Bruker PC software WINNMR-1D, Version 6.0, which is also available from Bruker Instruments, Inc. During data processing a line broadening of 1 Hz was applied to the data. Specific peaks were integrated in the region between 152 ppm and 142 ppm. The $^{13}$C NMR peak identifications of the chemical shifts of the benzylic carbons of the phenyl-alkane isomers is shown in Table 2.

TABLE 2

$^{13}$C NMR Peak Identifications

| Chemical Shift of the Benzylic Carbon (ppm) | Phenyl-alkane Isomer | Type of Quat |
|---|---|---|
| 149.6 | 2-methyl-2-phenyl | End |
| 148.3 | m-methyl-m-phenyl, m > 2 | Internal |
| 147.8 | m-methyl-2-phenyl, m ≠ 2 | NQ[1] |
| 146.2–146.3 | m-methyl-4-phenyl, m ≠ 4 | NQ[1] |
| 145.9 | m-methyl-3-phenyl, m ≠ 3 | NQ[1] |

[1]NQ = Nonquat

The 2-phenyl-alkane selectivity was computed by dividing the sum of the integral of the peak at 149.6 ppm and the integral of the peak at 147.8 ppm by the sum of the integrals of all of the peaks listed in Table 2, and multiplying by 100. The internal quaternary phenyl-alkane selectivity was computed by dividing the integral of the peak at 148.3 ppm by the sum of the integrals of all of the peaks listed in Table 2, and multiplying by 100. The results for the second liquid product are shown in Table 3.

After the period of 6 hours of collecting the second liquid product, the flow of combined feedstock to the reactor was maintained at a LHSV of 2.0 hr$^{-1}$ and the total pressure was maintained at 500 psi(g) (3447 kPa(g)). At these conditions, the reactor inlet temperature was increased from 150° C. (302° F.) to 175° C. (347° F.). The reactor lined out over a period of 12 hours with the combined feedstock passing to the reactor and contacting the extrudate at a LHSV of 2.0 hr$^{-1}$, a total pressure of 500 psi(g) (3447 kPa(g)), and a reactor inlet temperature of 175° C. (347° F.). At these conditions, a third liquid product was collected over the period of the next 6 hours. The third liquid product was analyzed by $^{13}$C NMR in the manner previously described. The results for the third liquid product are shown in Table 3.

TABLE 3

Liquid Product Analysis

| Reactor Inlet Temperature ° C. (° F.) | 2-Phenyl-Alkane Selectivity | Internal Quaternary Phenyl-Alkane Selectivity |
|---|---|---|
| 150 (302) | 66.4 | 4.6 |
| 175 (347) | 77.7 | 2.9 |

In the absence of shape selectivity, such as if an alkylation catalyst such as aluminum chloride or HF were used, most of the 2-methyl undecene would be expected to form 2-methyl-2-phenyl undecane (that is, an end quat). Likewise, most of the 6-methyl undecene, 5-methyl undecene, 4-methyl undecene, and 3-methyl undecene would be expected to form internal quats. The linear olefins would be expected to produce a statistical distribution of 2-phenyl-dodecane, 3-phenyl-dodecane, 4-phenyl-dodecane, 5-phenyl-dodecane, and 6-phenyl-dodecane. Thus, if the lights, the heavies, and the other alkyl olefins listed in Table 1 are excluded from the computations, the 2-phenyl-alkane selectivity would be no greater than 17 and the internal quaternary phenyl-alkane selectivity would approach 55. Table 3 shows the improvements which occur as a result of practicing this invention in which the alkylation of benzene occurs in the presence of NU-87. At both 150° C. (302° F.) and 175° C. (347° F.), Table 3 shows that the 2-phenyl-alkane selectivity is significantly higher than expected in the absence of shape selectivity and that the internal quaternary alkylbenzene selectivity obtained using shape-selective NU-87 zeolite is less than one-tenth of the internal quaternary alkylbenzene selectivity that would be expected in the absence of shape selectivity.

What is claimed is:

1. A process for producing arylalkanes, the process comprising contacting an olefin feed comprising monoolefin molecules having from about 8 to about 28 carbon atoms and having 3 or 4 primary carbon atoms with no guaternary carbon atoms with an aryl compound at alkylation conditions in the presence of a zeolite having an NES zeolite structure type, wherein the arylalkanes comprise molecules comprising one aliphatic alkyl portion and one aryl portion; the aliphatic alkyl portion has from about 8 to about 28 carbon atoms, has 2, 3, or 4 primary carbon atoms, and has no quaternary carbon atoms except for any quaternary carbon atom bonded by a carbon-carbon bond with a carbon atom of the aryl portion; and the process has a selectivity to 2-phenyl-alkanes of from 40 to 100 and a selectivity to internal quaternary phenyl-alkanes of less than 10.

2. The process of claim 1 wherein the monoolefin molecules have from 10 to 15 carbon atoms.

3. The process of claim 1 wherein the aliphatic alkyl portion has from 10 to 15 carbon atoms.

4. The process of claim 1 further characterized in that more than 70mol-% of the monoolefin molecules in the olefin feed having 3 or 4 primary carbon atoms with no quaternary carbon atoms comprise monoolefin molecules having 3 primary carbon atoms.

5. The process of claim 1 further characterized in that less than 25 mol-% of the monoolefin molecules in the olefin feed having 3 or 4 primary carbon atoms with no quaternary carbon atoms comprise monoolefin molecules having 4 primary carbon atoms.

6. The process of claim 1 wherein the aryl compound comprises a compound selected from the group consisting of benzene, toluene, and ethylbenzene.

7. The process of claim 1 further characterized in that the olefin feed comprises paraffin molecules, the paraffin molecules having from about 8 to about 28 carbon atoms.

8. The process of claim 1 further characterized in that the arylalkanes comprise molecules comprising one aryl portion and one aliphatic alkyl portion having a quaternary carbon atom bonded by a carbon-carbon bond with a carbon atom of the aryl portion.

9. The process of claim 1 further characterized in that the olefin feed comprises monoolefin molecules having at least one quaternary carbon atom, and the arylalkanes comprise molecules comprising one aryl portion and one aliphatic alkyl portion having a quaternary carbon atom not bonded by a carbon-carbon bond with a carbon atom of the aryl portion.

10. The process of claim 9 further characterized in that less than 1 mol-% of the monoolefin molecules in the olefin feed comprise monoolefin molecules having at least one quaternary carbon atom.

11. The process of claim 1 further characterized in that the olefin feed comprises monoolefin molecules comprising secondary carbon atoms and 2 primary carbon atoms, and the arylalkanes comprise molecules comprising one aryl portion and one aliphatic alkyl portion having 1 or 2 primary carbon atoms.

12. The process of claim 11 wherein the aliphatic alkyl portion has 2 primary carbon atoms.

13. The process of claim 11 further characterized in that no more than about 75 mol-% of the monoolefin molecules in the olefin feed comprise monoolefin molecules comprising secondary carbon atoms and 2 primary carbon atoms.

14. The process of claim 11 further characterized in that less than about 40 mol-% of the monoolefin molecules in the olefin feed comprise monoolefin molecules comprising secondary carbon atoms and 2 primary carbon atoms.

15. The process of claim 1 further characterized in that the alkylation conditions comprise a temperature of from about 80 to about 200° C. and a pressure sufficient to maintain a liquid phase or supercritical conditions.

16. The process of claim 1 wherein the zeolite comprises NU-87 or gottardiite.

17. The process of claim 1 wherein the monoolefin molecules comprise monomethyl-alkenes.

18. The process of claim 1 wherein the arylalkanes comprise monomethyl-arylalkanes.

* * * * *

UNITED STATES PATENT AND TRADEMARK OFFICE
CERTIFICATE OF CORRECTION

PATENT NO.: 6,111,158
DATED: August 29, 2000
INVENTORS: Richard E. Marinangeli et al.

It is certified that error appears in the above-identified patent and that said Letters Patent is hereby corrected as shown below:

In column 18, line 44, "guaternary" should be replaced with "quaternary."

Signed and Sealed this

Fifteenth Day of May, 2001

Attest:

NICHOLAS P. GODICI

Attesting Officer

Acting Director of the United States Patent and Trademark Office